United States Patent [19]

Zeng et al.

[11] Patent Number: 5,700,875
[45] Date of Patent: Dec. 23, 1997

[54] ADHESIVE COMPOSITION FOR DENTAL TREATMENT

[75] Inventors: Weiping Zeng; Takashi Yamamoto; Masami Arata; Tsuyoshi Banba, all of Moriyama, Japan

[73] Assignee: Sun Medical Co., Ltd., Moriyama, Japan

[21] Appl. No.: 445,959

[22] Filed: May 22, 1995

[30] Foreign Application Priority Data

May 25, 1994 [JP] Japan .................. 6-110673
Oct. 19, 1994 [JP] Japan .................. 6-253802

[51] Int. Cl.$^6$ .................. A61K 6/08; C08F 765/02
[52] U.S. Cl. .................. 525/301; 525/328; 433/10
[58] Field of Search .................. 525/301; 526/328; 433/10

[56] References Cited

U.S. PATENT DOCUMENTS 4,380,432  4/1983  Orlowski et al. .................. 433/9

FOREIGN PATENT DOCUMENTS 0051796   5/1982   European Pat. Off. .
0266220   5/1988   European Pat. Off. .
0282280   9/1988   European Pat. Off. .
0567213   10/1993  European Pat. Off. .
58-79911  5/1983   Japan .
2256875   12/1992  United Kingdom .
9424985   11/1994  WIPO .

OTHER PUBLICATIONS

Database WPI, Section CH, Week 9523, Derwent Publications Ltd., London, GB Class A96, AN 95–175314 & JP–A 07 097 306 (San Medical KK) 11 Apr. 1995.

*Primary Examiner*—Irina S. Zemel
*Attorney, Agent, or Firm*—Sherman and Shalloway

[57] ABSTRACT

An adhesive composition comprising (A) 98 to 60 parts by weight of a polymerizable monomer mixture containing 2 to 25% by weight of a monomer having acidic group, (B) 2 to 40 parts by weight of a polymer, preferably a polymer which can form a solution or dispersion having the property that the solution or dispersion of 10 parts by weight of the polymer in 90 parts by weight of methyl methacrylate shows a viscosity of 100 cps or less at 25° C., and (C) 0.01 to 35 parts by weight of a polymerization initiator, provided that the total amount of the components (A), (B) and (C) is 100 parts by weight.

According to the present invention, there can be provided an adhesive composition which is easy to handle for the restoration treatment of a tooth, so that adhesion dental treatment can be reliably carried out.

12 Claims, No Drawings

ADHESIVE COMPOSITION FOR DENTAL TREATMENT

DETAILED DESCRIPTION OF THE INVENTION

The present invention relates to an adhesive composition for dental treatment. More specifically, the present invention relates to an adhesive composition for dental treatment which contains (A) a polymerizable monomer mixture containing a monomer having an acidic group, (B) a specific polymer, (C) a polymerization initiator and optionally, (D) a filler and which is easy to handle in dental treatment and exhibits excellent adhesion performance and an excellent restoration effect when a tooth and a restoration material are bonded to each other.

In the field of dental treatment, it is required to firmly bond a tooth and a tooth-restoring material (e.g., a polymer, a metal or a ceramic) to each other, and various adhesives therefor have been proposed.

The above adhesive compositions are generally composed of four components such as (1) a polymerizable monomer, (2) an adhesion-promoting monomer or a monomer having affinity with a tooth, (3) a polymerization catalyst or a polymerization initiator and (4) an inorganic or organic filler.

As typical examples of the above adhesive compositions, there have been proposed an adhesive composition containing, as a polymerization catalyst or a polymerization initiator, a mixture of a photosensitizer selected from diketones with a reducing agent selected from amines, and a chemically curable adhesive composition containing, as a polymerization catalyst or a polymerization initiator, a mixture of benzoyl peroxide with an aromatic tertiary amine or tributylborane partial oxide (TBBO).

Concerning the above known adhesive compositions, it has been clinically confirmed that an adhesive composition containing TBBO as a polymerization initiator has high adhesion strength and less harmfulness to a human body.

Of the above prior art technique, an adhesive composition containing TBBO is the most excellent. But, this adhesive composition is composed of three separate portions in form, i.e., a polymer powder, a monomer liquid and a catalyst liquid. When this composition is prepared for use, the viscosity of the composition rapidly increases, and the period of time available for the application of the composition to a tooth and a restoration material after the initiation of the mixing of the above components, i.e., the operationable time, is considerably short, and it is therefore pointed out that the above composition is inconvenient in use. Further, the preparation of the above composition requires operation procedures of weighing and mixing a predetermined amount of the monomer liquid and a predetermined amount of the polymer powder and incorporating a predetermined amount of the catalyst to the mixture.

It is therefore desired to develop an adhesive composition which has excellent handling properties and exhibits reliable adhesion performance.

It is an object of the present invention to provide an adhesive composition which has excellent handling properties and exhibits excellent adhesion performance.

The above object and advantages of the present invention are achieved by the use of an adhesive composition comprising (A) 98 to 60 parts by weight of a polymerizable monomer mixture containing 2 to 20% by weight of a monomer having acidic group, (B) 2 to 40 parts by weight of a polymer, and (C) 0.01 to 85 parts by weight of a polymerization initiator, provided that the total amount of the components (A), (B) and (C) is 100 parts by weight.

When the adhesive composition of the present invention is used for bonding a tooth and a restoration material to each other, the operation procedures are easy, and the adhesion performance and the restoration effect are greatly improved, so that the above problems can be overcome.

In the adhesive composition of the present invention, the component (A) is a polymerizable monomer mixture containing 2 to 20% by weight of a monomer having acidic group. A monomer other than the monomer having acidic group is not specially limited, and can be selected from generally known monofunctional monomers and polyfunctional monomers. Particularly preferred is a (meth)acrylate-containing monomer which has relatively low stimulus to a human body. Specific examples thereof are as follows.

(A) Specific examples of the monofunctional monomers as component (A) include alkyl esters of (meth)acrylic acids such as methyl (meth)acrylate, ethyl (meth)acrylate, butyl (meth)acrylate, hexyl (meth)acrylate, 2-ethylhexyl (meth)acrylate, dodecyl (meth)acrylate, lauryl (meth)acrylate, cyclohexyl (meth)acrylate, benzyl (meth)acrylate, isobornyl (meth)acrylate and adamantyl (meth)acrylate;

hydroxyalkyl esters of the (meth)acrylic acids such as 2-hydroxyethyl (meth)acrylate, 2- or 8-hydroxypropyl (meth)acrylate, 4-hydroxybutyl (meth)acrylate, 5-hydroxypentyl (meth)acrylate, 6-hydroxyhexyl (meth)acrylate, 1,2- or 1,8-dihydroxypropyl mono(meth)acrylate and erythritol mono(meth)acrylate;

polyethylene glycol mono(meth)acrylates such as diethylene glycol mono(meth)acrylate, triethylene glycol mono(meth)acrylate, polyethylene glycol mono(meth)acrylate and polypropylene glycol mono(meth)acrylate;

fluoroalkyl esters of (meth)acrylic acids such as perfluorooctyl (meth)acrylate and hexafluorobutyl (meth)acrylate;

silane compounds having (meth)acryloxyalkyl group such as γ-(meth)acryloxypropyltrimethoxysilane, and γ-(meth)acryloxypropyl(trimethylsiloxy)silane; and (meth)acrylates having heterocyclic ring such as tetrafurfuryl (meth)acrylate.

The above monofunctional monomers may be used alone or in combination. The monofunctional monomer is used usually in an amount of 5 to 60% by weight, preferably 8 to 55% by weight, based on the polymerizable monomer mixture.

Specific examples of the polyfunctional monomers as component (A) include poly(meth)acrylates of alkane polyols such as ethylene glycol di(meth)acrylate, propylene glycol di(meth)acrylate, butylene glycol di(meth)acrylate, neopentyl glycol di(meth)acrylate, hexylene glycol di(meth)acrylate, trimethylolpropane tri(meth)acrylate and pentaerythritol tetra(meth)acrylate;

poly(meth)acrylates of polyoxyalkanepolyols such as diethylene glycol di(meth)acrylate, triethylene glycol di(meth)acrylate, polyethylene glycol di(meth)acrylate, dipropylene glycol di(meth)acrylate, polypropylene glycol di(meth)acrylate and dipentaerythritol hexa(meth)acrylate;

aromatic di(meth)acrylates such as 2,2-bis{4-(meth)acryloxyphenyl}propane, 2,2-bis{4-(meth)acryloxyethoxyphenyl}propane, 2,2-bis{4-(meth)acryloxydiethoxyphenyl}propane, 2,2-bis{4-(meth)acryloxytriethoxyphenyl}propane, 2,2-bis{4-(meth)acryloxypolyethoxyphenyl}propane, 2,2-bis{4-[3-(meth)acryloxy]-2-hydroxypropoxyphenyl}propane;

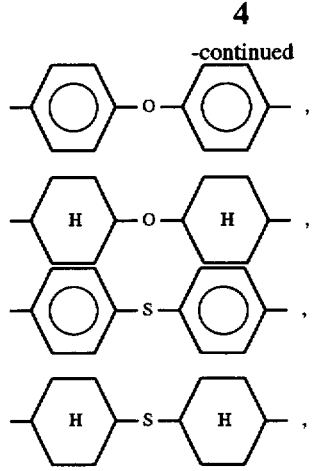

aliphatic or aromatic epoxydi(meth)acrylate of the formula (2)

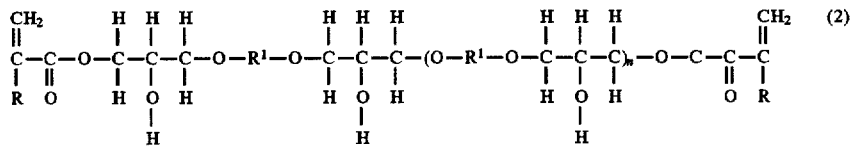

aliphatic or aromatic di(meth)acrylate of the formula (1),

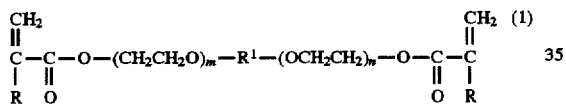

wherein R is hydrogen or methyl, each of m and n is 0 or a positive number, and R¹ is

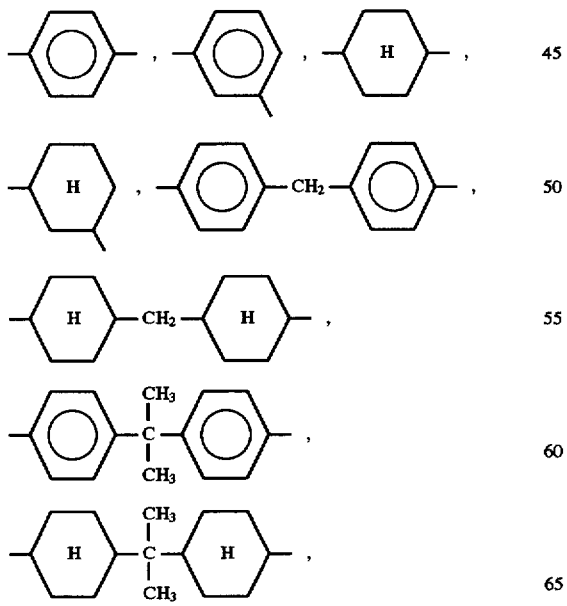

wherein R is hydrogen or methyl, n is 0 or a positive number, and R¹ is —(CH$_2$)$_2$—, —(CH$_2$)$_4$—,

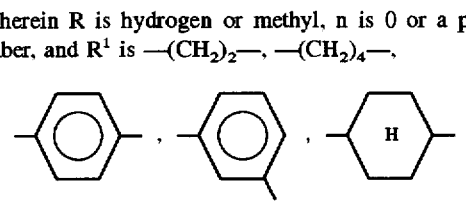

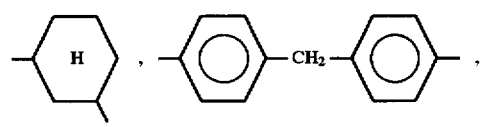

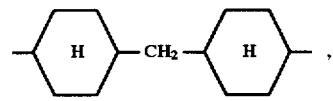

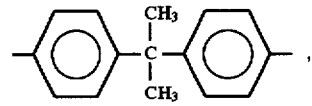

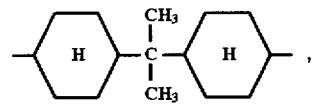

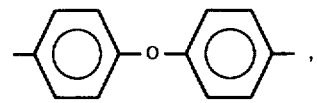

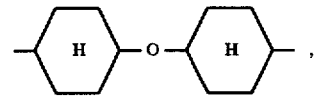

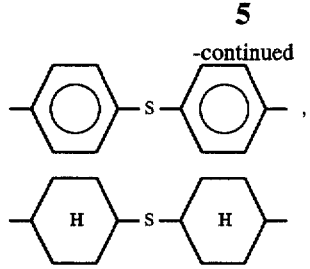

polyfunctional (meth)acrylates of which the molecule has urethane bond, of the formula (3),

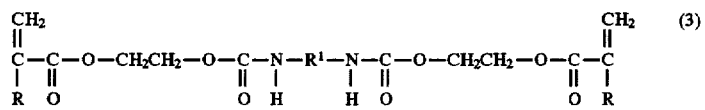

wherein R is hydrogen or methyl and $R^1$ is —$(CH_2)_2$—, —$(CH_2)_4$—, —$(CH_2)_6$—,

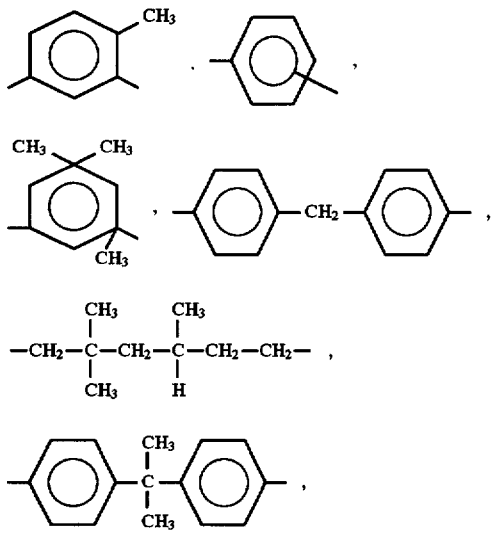

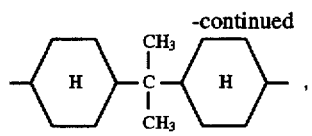

Of the above monomers, particularly preferred as a monofunctional monomer are alkyl (meth)acrylates such as methyl (meth)acrylate and ethyl (meth)acrylate, (meth)acrylate containing hydroxyl group such as 2-hydroxyethyl (meth)acrylate, 1,3-dihydroxypropyl mono(meth)acrylate and erythritol mono(meth)acrylate, and (meth)acrylates of which the molecule contains ethylene glycol chain such as triethylene glycol monomethyl ether (meth)acrylate and triethylene glycol mono(meth)acrylate.

In these monomers, (meth)acrylate containing hydroxyl group or (meth)acrylate having ethylene glycol chain in the molecule is used preferably in an amount of 5 to 30% by weight, more preferably 8 to 25% by weight, based on the polymerizable monomer mixture.

Particularly preferred as a polyfunctional monomer are di(meth)acrylates of which the molecule contains ethylene glycol chain such as triethylene glycol di(meth)acrylate and polyethylene glycol di(meth)acrylate, a compound of the formula (4),

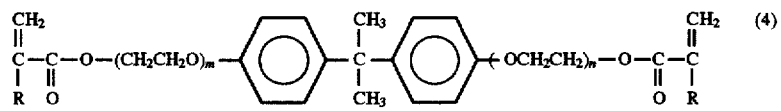

wherein R is hydrogen or methyl and each of m and n is independently an integer of at least 1, provided that m+n equals 2 to 20, a compound of the formula (5),

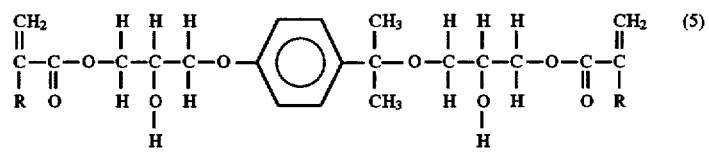

wherein R is hydrogen or methyl, and a compound of the formula (6),

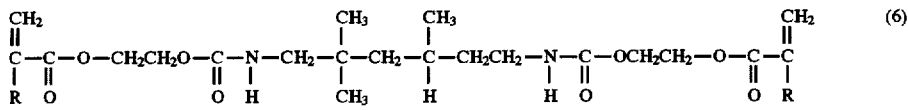

wherein R is hydrogen or methyl.

The polyfunctional (meth)acrylate monomer is used preferably in an amount of 10 to 50% by weight, more preferably 20 to 45% by weight, based on the polymerizable monomer mixture.

The above monofunctional and polyfunctional (meth) acrylate monomers may be used alone or in combination. Further, the other monomers such as styrene, α-methyl vinyl styrene and p-methylsytrene may be used so long as the object of the present invention is not impaired.

Specific examples of the polymerizable monomer of which the molecule contains acidic group include monomers containing carboxyl group or its anhydride such as (meth)acrylic acid and its anhydride, 1,4-di(meth) acryloxyethylpyromellitic acid, 6-(meth) acryloxyethylnaphthalene 1,2,6-tricarboxylic acid, N-(meth)acryloyl-p-aminobenzoic acid, N-(meth)acryloyl-o-aminobenzoic acid, N-(meth)acryloyl-m-aminobenzoic acid, N-(meth)acryloyl-5-aminosalicylic acid, N-(meth) acryl-4-aminosalicylic acid, 4-(meth) acryloxyethyltrimellitic acid and its anhydride, 4-(meth) acryloxybutyltrimellitic acid (4-MET) and its anhydride (4-META), 4-(meth)acryloxyhexyltrimellitic acid and its anhydride, 4-(meth)acryloxydecyltrimellitic acid and its anhydride, 2-(meth)acryloyloxybenzoic acid, 3-(meth) acryloxybenzoic acid, 4-(meth)acryloxybenzoic acid, β-(meth)acryloyloxyethyl hydrogensuccinate, β-(meth) acryloxyethyl hydrogenmaleate, β-(meth)acryloyloxyethyl hydrogenphthalate, 11-(meth)acryloxyoxy-1,1-undecanedicarboxylic acid and p-vinylbenzoic acid;

monomers containing phosphoric acid group such as (2-(meth)acryloxyethyl)phosphoric acid, (2-(meth) acryloxyethylphenyl)phosphoric acid and 10-(meth) acryloxydecylphosphoric acid; and monomers containing sulfonic acid group such as p-styrenesulfonic acid and 2-acrylamide-2-methylpropanesulfonic acid.

The above monomers containing acidic group may be used alone or in combination. Of these monomers containing acidic group, 4-MET and 4-META are preferred. The amount of the monomer containing acidic group is preferably 2 to 20 parts per 100 parts by weight of the total amount of polymerizable monomer components.

The amount of the polymerizable monomer (A) per 100 parts by weight of the total amount of the components (A), (B) and (C) is generally in the range of from 98 to 60 parts by weight, preferably in the range of from 95 to 70 parts by weight.

In the adhesive composition of the present invention, the polymer as component (B) is a polymer which can form a solution or dispersion having the property that the solution or dispersion of 10 parts by weight of the polymer in 90 parts by weight of methyl methacrylate generally shows a viscosity, at 25° C., of 100 cps or less, preferably a viscosity, at 25° C., of 70 cps or less, particularly preferably a viscosity, at 25° C., of 50 cps or less. When this polymer is dissolved or dispersed in the polymerizable monomer (A), this polymer does not increase the viscosity of the mixture so that it does not prevent the penetration of the adhesive composition into a tooth and provides an excellent adhesion effect.

Examples of the polymer as component (B) include a copolymer ("MSH copolymer" hereinafter) obtained from alkyl (meth)acrylate, a styrene monomer and a hydroxyalkyl (meth)acrylate of which the molecule contains at least one hydroxyl group; a copolymer ("MS copolymer" hereinafter) obtained from alkyl (meth)acrylate and a styrene monomer; a copolymer ("MSB copolymer" hereinafter) obtained from alkyl (meth)acrylate, a styrene monomer and butadiene; polyalkyl methacrylate; and polyvinyl acetate.

Examples of the alkyl (meth)acrylate for the copolymers as component (B) include methyl (meth)acrylate, ethyl (meth)acrylate, propyl (meth)acrylate, butyl (meth)acrylate, hexyl (meth)acrylate and 2-ethylhexyl (meth)acrylate. Of these, particularly preferred are methyl (meth)acrylate and ethyl (meth)acrylate. These alkyl (meth)acrylates may be used alone or in combination.

Examples of the styrene monomer include styrene, α-methylstyrene and p-methylstyrene. Of these, styrene and p-methylstyrene are particularly preferred. These styrene monomers may be used alone or in combination.

Examples of the hydroxyalkyl (meth)acrylate for the copolymers as component (B) include 2-hydroxyethyl (meth)acrylate, 2- or 3-hydroxypropyl (meth)acrylate, 4-hydroxybutyl (meth)acrylate, 5-hydroxypentyl (meth) acrylate, 6-hydroxyhexyl (meth)acrylate and 1,2- or 1,3-dihydroxypropane (meth)acrylate. Of these, particularly preferred are 2-hydroxyethyl (meth)acrylate and 2- or 3-hydroxypropyl (meth)acrylate. These hydroxyalkyl (meth)acrylates may be used alone or in combination.

In the MSH copolymer (b1) as component (B), the content of the alkyl (meth)acrylate is 30 to 70% by weight, the content of the styrene or styrene derivative is 20 to 60% by weight, and the content of the hydroxyalkyl (meth)acrylate is 5 to 30% by weight.

In the MS copolymer (b2) as component (B), the content of the alkyl (meth)acrylate is 30 to 70% by weight, and the content of the styrene monomer is 70 to 30% by weight.

In the MSB copolymer (b3) as component (B), the content of the alkyl (meth)acrylate is 5 to 3% by weight, the content of the styrene monomer is 15 to 40% by weight, and the content of butadiene is 40 to 70% by weight. The MSB copolymer is an elastomer and forms dispersion in methyl methacrylate.

In the alkyl (meth)acrylate polymer (b5) as component (B), the content of alkyl (meth)acrylate is 50 to 100% by weight, and the content of other alkyl (meth)acrylate is 0 to 50% by weight.

In the adhesive composition of the present invention, the amount of the polymer (B) per 100 parts by weight of the total amount of the components (A), (B) and (C) is generally in the range of from 2 to 40 parts by weight, preferably in the range of from 5 to 30 parts by weight.

In the adhesive composition of the present invention, polymers including the MSH copolymer, the MS copolymer, the MSB copolymer, the alkyl (meth)acrylate polymer and the polyvinyl acetate may be used alone or combination, and when at least one of these polymers is dissolved and/or dispersed in the polymerizable monomer for the composition, the polymers can form a mixed liquid which can be stably stored without causing no great viscosity increase and can retain the performance of the composition penetrating a tooth. Further, when the polymer is co-present in the composition, the content of polyfunctional monomer can be decreased without impairing the curability of the composition, so that the composition can be improved in handling properties and can exhibit excellent adhesion performance and an excellent restoration effect when a tooth and a restoration material are bonded to each other.

In the adhesive composition of the present invention, the component (C) is a polymerization initiator and can be selected from known peroxides, photopolymerization initiators, trialkylborane and partial oxide of trialkylborane.

Examples of the peroxides as component (C) include organic peroxides such as diacetylpentyl peroxide, dipropyl peroxide, dibutyl peroxide, dicapryl peroxide, benzoyl peroxide (BPO), p,p'-dichlorobenzoyl peroxide, p,p'-dimethoxybenzoyl peroxide and p,p'-dimethylbenzoyl peroxide. Of these, BPO is preferred. Further, examples of the peroxides as component (C) include inorganic peroxides such as ammonium persulfate, potassium persulfate, potassium chlorate, potassium bromate and potassium perphosphate. The amount of the peroxide per 100 parts by weight of the total amount of the component (A), (B) and (C) is generally in the range of from 0.01 to 10 parts by weight, preferably in the range of from 0.1 to 5 parts by weight.

The photopolymerization initiators as component (C) are not specially limited so long as they have the capability of photopolymerization initiation when exposed to ultraviolet light or visible light. Examples of the photopolymerization initiators include ultraviolet light or visible light sensitizers such as benzyl, 4,4'-dichlorobenzyl, benzoin, benzoin methyl ether, benzoin ethyl ether, benzoin isopropyl ether, benzophenone, diacetyl, d,1-camphorquinone (CQ), camphorquinone-10-sulfonic acid, camphorquinone-10-carboxylic acid, 2,4-diethylthioxanthone and 2,4,6-trimethylbenzoyldiphenylphosphine oxide. The above photopolymerization initiators may be used alone or in combination. The amount of the photopolymerization initiator per 100 parts by weight of the total amount of the components (A), (B) and (C) is generally in the range of from 0.01 to 10 parts by weight, preferably in the range of from 0.1 to 5 parts by weight.

For improving the polymerization initiation effect of the above peroxide or photopolymerization initiator, it is preferred to use a polymerization promoter such as a reducing compound in combination. Examples of the polymerization promoter that can be used in combination include organic reducing compounds such as N,N-dimethylaniline, N,N-dimethyl p-toluidine (DMPT), N,N-diethyl p-toluidine, N,N-diethanol p-toluidine (DEPT), N,N-dimethyl p-tert-butylaniline, N,N-dimethylanasidine, N,N-dimethyl p-chloroaniline, N,N-dimethylaminethyl (meth) acrylate, N,N-diethylaminoethyl (meth)acrylate, N,N-dimethylbenzoic acid and its alkyl ester, N,N-diethylbenzoic acid (DEABA) and its alkyl ester, N,N-dimethylaminobenzaldehyde (DMABAd), N-phenylglycine (NPG), N-tolylglycine (NTG), N,N-(3-methacryloyloxy-2-hydroxypropyl)phenylglycine (NPG-GMA) and glutaraldehyde, inorganic reducing compounds such as sulfurous acid, bisulfurous acid, metasulfurous acid, metabisulfurous acid, pyrosulfurous acid, thiosulfuric acid, dithionic acid, hyposulfurous acid, hydrosulfurous acid and salts of these, and aromatic sulfinic acids such as benzenesulfinic acid, o-toluenesulfinic acid, p-toluenesulfinic acid, ethylbenzenesulfinic acid, decylbenzenesulfinic acid, decylbenzenesulfinic acid, chlorobenzenesulfinic acid and naphthalenesulfinic acid or salts of these.

The amount of the above polymerization promoter such as reducing compound and aromatic sulfinic acid or salts thereof per 100 parts by weight of the total amount of the components (A), (B) and (C) is generally in the range of from 0.01 to 10 parts by weight, preferably in the range of from 0.1 to 5 parts by weight.

The trialkylborane or the partial oxide of trialkylborane is selected from triethylborane, tripropylborane, triisopropylborane, tri-n-butylborane, triisobutylborane, tri-sec-butylborane, tri-n-amylborane, tri-3-amylborane, triisoamylborane, tri-sec-amylborane and trialkylborane oxides which are partial oxides of these. Of these, preferred is tri-n-butylborane or its partial oxide. The amount of the above trialkylborane or the partial oxide of trialkylborane per 100 parts by weight of the total amount of the components (A), (B) and (C) is generally in the range of from 2 to 35 parts by weight, preferably in the range of from 5 to 30 parts by weight.

Of the above polymerization initiators, preferred is trialkylborane, a partial oxide of trialkylborane or a photopolymerization initiator.

The adhesive composition of the present invention may further contain a filler as component (D). The filler is generally selected from known inorganic fillers and known organic fillers.

Examples of the inorganic fillers as component (D) include metal oxides such as zirconium oxide, bismuth oxide, titanium oxide, zinc oxide and aluminum oxide, metals salts such as calcium carbonate, bismuth carbonate, calcium phosphate, zirconium phosphate and barium phosphate, and glass fillers such as a silica glass filer, a barium-containing glass filler, a strontium-containing glass filler and a zirconia silicate glass filler. Organic composite fillers are also used. The above inorganic fillers may be used alone or in combination.

For decreasing the thickness of a coating of the adhesive composition and improving the restoration effect of the adhesive composition, the average particle diameter of the above inorganic filler is generally in the range of from 0.001 to 50 μm, preferably in the range of from 0.005 to 30 μm.

Further, for achieving strong adhesion between the filler and a resin, the above filler is preferably surface-treated with silane, polymer-coated, or the like.

Examples of the organic filler as component (D) include metal organic compounds such as an organic bismuth compound, an organic zirconium compound and an organic titanium compound. The above organic fillers may be used alone or in combination.

The above inorganic fillers and the above organic fillers may be used in combination. The inorganic filler is preferred for improving the cured adhesive composition in mechanical properties.

The amount of the filler per 100 parts by weight of the total of the components (A), (B) and (C) is preferably in the range of from 25 to 400 parts by weight, more preferably in the range of from 30 to 300 parts by weight.

When the adhesive composition of the present invention contains the components (A) and (B) or the components (A), (B) and (C), the viscosity of the composition is preferably 1,000 cps or less, more preferably 500 cps or less, particularly preferably 200 cps or less at 37.5° C. When the above adhesive composition further contains the component (D), the composition can be used without any limitation so long as the composition containing the components (A), (B) and (C) shows the above viscosity. In this case, the composition is preferably in the state of a paste.

The adhesive composition of the present invention can be stored in any combinations or proportions of the components (A), (B) and (C) or the components (A), (B), (C) and (D). For examples, the components can be divided to at least two liquids or paste-like compositions such as ((A)+(B)) and (C); ((A)+(B)+(D)) and (C); or ((A)+(B)+(C)) and ((A)+(B) +polymerization promoter), and these divided compositions can be stored as such.

The adhesive composition of the present invention may contain proper amounts of a colorant, a hydroquinone polymerization inhibitor or a solvent as required.

EXAMPLES

The present invention will be explained with reference to Examples hereinafter, while the present invention shall not be limited to these Examples.

Examples 1–10

Predetermined amounts of a polymerizable monomer and a polymer powder shown in Table 1 were weighed, and these components were mixed to prepare a solution or a dispersion. Then, the resultant mixture of the polymer with the monomer was measured for a viscosity at 25° C. by using a Ubbelohd's viscosity in Examples 1 to 4, and at 37.5° C. by using a E-type viscometer (type EHD, supplied by TOKIMEC Co., Ltd.) in Examples 5 to 10. Table 1 shows the results.

TABLE 1

| | Composition | Viscosity |
|---|---|---|
| Example 1 | MMA: 9 g, MSH: 1 g | 9 |
| Example 2 | MMA: 9 g, PMS: 1 g | 8 |
| Example 3 | MMA: 9 g, MSB: 1 g | 3 |
| Example 4 | MMA: 9 g, PVAc: 1 g | 13 |
| Example 5 | MMA: 9 g, PMMA: 0.5 g MSB: 0.5 g | 40 |
| Example 6 | 2.6E: 2.5 g, HEMA: 1.5 g 4-META: 1 g, MMA: 4 g MSH: 1 g | 85 |
| Example 7 | 2.6E: 2.5 g, HEMA: 1.5 g 4-META: 1 g, MMA: 4 g PMS: 1 g | 72 |
| Example 8 | 2.6E: 2.5 g, HEMA: 1.5 g 4-META: 1 g, MMA: 4 g MSB: 1 g | 35 |
| Example 9 | 2.6E: 2.5 g, HEMA: 1.5 g 4-META: 1 g, MMA: 4 g PVAc: 1 g | 115 |
| Example 10 | 2.6E: 2.5 g, HEMA: 1.5 g | 120 |

TABLE 1-continued

| Composition | Viscosity |
|---|---|
| 4-META: 1 g, MMA: 4 g PMMA: 0.5 g, MSB 0.5 g | |

The abbreviations used in Table 1 refer to the following compounds.

MMA: methyl methacrylate

HEMA: 2-hydroxyethyl methacrylate 2,6E: 2,2-bis[(4-methacryloxyethoxy)phenyl]-propane 4-META: 4-methacryloxyethyltrimellitic acid anhydride MSH: methyl methacrylate.styrene.2-hydroxyethyl methacrylate copolymer powder PMS: methyl methacrylate.styrene copolymer powder (HI-PEARL D-1955MSL, supplied by Negami Chemical Industries Co., Ltd)

MSB: methyl methacrylate.butadiene.styrene copolymer powder (BTA 705, supplied by Kureha KK)

PVAc: polyvinyl acetate powder (SAKUNOHOL DR-117, supplied by Denki Kagaku KK)

PMMA: polymethyl methacrylate (HI-PEARL D250ML, supplied by Negami Chemical Industries Co., Ltd)

Examples 11–17 and Comparative Examples 1–2

Predetermined amounts of components for a composition in the state of a liquid, a paste or a powder, shown in Table 2, were taken out and mixed at room temperature. The mixture (composition) was evaluated for handling properties by measuring a time until the composition gelled (available period of time) and a time until a needle (ø: 0.5 mm) no longer penetrated the composition (cure time). Table 2 shows the results.

TABLE 2

| | Composition [(value in parenthesis) = part by weight] | Available period of time (second) | Cure time (minute) | How many times quantitative determination carried out |
|---|---|---|---|---|
| Ex. 11 | Mixture liquid: 0.1 g (2.6E: 25, HEMA: 15, MMA: 40, 4-META: 10, MSH: 10) TBBO: 0.016 g | 70 | 12 | 2 |
| Ex. 12 | Mixture liquid: 0.1 g (2.6E: 25, HEMA: 15, MMA: 40, | 65 | 11 | 2 |

TABLE 2-continued

| | Composition [(value in parenthesis) = part by weight] | Available period of time (second) | Cure time (minute) | How many times quantitative determination carried out |
|---|---|---|---|---|
| | 4-META: 10, PMS: 10) TBBO: 0.016 g | | | |
| Ex. 13 | Mixture liquid: 0.1 g (2.6E: 25, HEMA: 15, MMA: 40, 4-META: 10, MSB: 10) TBBO: 0.016 g | 70 | 11 | 2 |
| Ex. 14 | Mixture liquid: 0.1 g (2.6E: 25, HEMA: 15, MMA: 40, 4-META: 10, PMS: 5, MSB: 5) TBBO: 0.016 g | 70 | 11 | 2 |
| Ex. 15 | Mixture liquid: 0.1 g (2.6E: 25, HEMA: 15, MMA: 40, 4-META: 10, PMMA: 5, MSB: 5) TBBO: 0.016 g | 65 | 12 | 2 |
| Ex. 16 | Mixture liquid: 0.1 g (2.6E: 25, HEMA: 15, MMA: 40, 4-META: 10, PVAc: 10) TBBO: 0.016 g | 70 | 12 | 2 |
| Ex. 17 | Paste: 0.25 g (2.6E: 15, HEMA: 10, MMA: 15, 4-META: 5, MSB: 15, GBa: 40) TBBO: 0.008 g | 65 | 12 | 2 |
| C Ex. 1 | Mixture liquid: 0.1 g (2.6E: 30, HEMA: 15, MMA: 45, 4-META: 10) TBBO: 0.016 g | 45 | 13 | 2 |
| C Ex. 2 | Mixture liquid: 0.08 g (MMA: 95, 4-META: 5) PMMA powder: 0.08 g TBBO: 0.016 g | 45 | 14 | 3 |

Ex. = Example, C Ex. = Comparative Example

The abbreviations used in Table 2 refer to the following compounds.

TBBO: partial oxide of tributylborane (catalyst), supplied by Sun Medical Co., Ltd)

GBa: barium-containing glass powder (8235G, supplied by Sun Medical Co., Ltd)

For the remaining abbreviations, see notes to Table 1.

Examples 18–27

A bovine anterior tooth on a lip side was cut to expose enamel (E) or dentin (D), and the enamel or the dentin was polished with No. 600 emery paper to prepare an adhesion surface.

The above adhesion surface was washed with water and dried. Then, the dry adhesion surface was treated with an etching aqueous solution containing 3% by weight of iron chloride and 10% by weight of citric acid for 30 second, washed with water for 20 seconds, and dried by air-blowing for 15 seconds. Then, a Cellophane tape having a circular hole having a diameter of 4 mm was attached to the adhesion surface to define an adhesion area. In Example 18, an adhesive composition of the present invention shown in Table 3 was applied to the above adhesion surface, and a SUS rod was bonded thereon to prepare an adhesion test sample.

In Examples 19 to 24, an adhesive composition of the present invention shown in Table 3 was applied to the above area-defined adhesion surface and moderately air-blown to form a uniform coating of the adhesive composition, and the coating was allowed to stand for about 30 seconds. Then, a 1 mm thick Teflon mold having a hole having a diameter of 5 mm was attached to the adhesion surface. A composite resin for dental treatment (Silux Plus, supplied by 3M) was filled in the hole portion, and irradiated with visible light with a visible light irradiator for dental treatment (Translux, supplied by Kulzer) at a distance of 5 mm for 40 seconds to cure the composite resin. A rod of polymethyl methacrylate (PMMA) was bonded to the cured composite resin with a fast-curable immediately polymerizable resin (Metafast, supplied by Sun Medical Co., Ltd) to prepare an adhesion test sample.

In Examples 25 to 27, a primer solution containing 1.5 g of 4-META, 1.5 g of polyethylene glycol dimethacrylate (23 G, supplied by Shin-nakamura Chemical Co., Ltd), 7 g of ethanol, 10 g of water, 0.01 g of camphorquinone and 0.01 g of N,N'-dimethylaminobenzoic acid was applied to the above adhesion surface formed by polishing the above enamel or dentin with No. 600 emery paper, and after 40 seconds, the resultant primer coating was air-blown with an air gun. Then, a Cellophane tape having a hole having a diameter of 4 mm was attached to the adhesion surface to define an adhesion area. An adhesive composition of the present invention shown in Table 3 was applied to the primer, and irradiated with visible light with a visible light irradiator for dental treatment (Translux, supplied by Kulzer) at a distance of 5 mm for 20 seconds. Then, a 1 mm thick Teflon mold having a hole having a diameter of 5 mm was attached to the adhesion surface. A composite resin for dental treatment (Silux Plus, supplied by 3M) was filled in the hole portion, and irradiated with visible light with the visible light irradiator for dental treatment at a distance of 5 mm for 40 seconds to cure the composite resin. A rod of polymethyl methacrylate (PMMA) was bonded to the cured composite resin with a fast-curable immediately polymerizable resin (Metafast, supplied by Sun Medical Co., Ltd) to prepare an adhesion test sample. The adhesion test sample was allowed to stand at room temperature for 30 minutes, immersed in distilled water at 37° C. for 24 hours and subjected to a tensile test for an adhesion strength between the acryl rod and the tooth. The adhesion strength is an average of measurement values of five samples.

Table 3 shows the adhesion strength values measured in the above manner.

TABLE 3

| | Composition (part by weight) | | Adhesion strength (MPa) |
|---|---|---|---|
| Example 18 | 2.6E: 15, MMA: 15, MSB: 15, | HEMA: 10, 4-META: 5, GBa: 40, TBBO: 5 | E: 14.2 D: 15.3 |
| Example 19 | 2.6E: 25, MMA: 40, MSH: 10, | HEMA: 15, 4-META: 10, TBBO: 16 | E: 14.2 D: 15.1 |
| Example 20 | 2.6E: 25, MMA: 40, PMS: 10, | HEMA: 15, 4-META: 10, TBBO: 16 | E: 13.4 D: 14.2 |
| Example 21 | 2.6E: 25, MMA: 40, MSB: 10, | HEMA: 15, 4-META: 10, TBBO: 16 | E: 14.2 D: 15.7 |
| Example 22 | 2.6E: 25, MMA: 40, MS: 5, | HEMA: 15, 4-META: 10, MSB: 10, TBBO: 16 | E: 14.0 D: 15.2 |
| Example 23 | 2.6E: 25, MMA: 40, PMMA: 5, | HEMA: 15, 4-META: 10, MSB: 10, TBBO: 16 | E: 13.0 D: 13.7 |
| Example 24 | 2.6E: 25, MMA: 40, PVAc: 10, | HEMA: 15, 4-META: 10, TBBO: 16 | E: 13.9 D: 15.1 |
| Example 25 | 2.6E: 20, MMA: 25, CQ: 0.5 | 3G: 20, HEMA: 20, MSH: 10, 4-MET: 4, DEABA: 0.7 | E: 11.5 D: 14.8 |
| Example 26 | 2.6E: 20, MMA: 25, CQ: 0.5 | 3G: 20, HEMA: 20, PMS: 10, 4-MET: 4, DEABA: 0.7 | E: 10.8 D: 12.8 |
| Example 27 | 2.6E: 20, MMA: 25, CQ: 0.5 | 3G: 20, HEMA: 20, MSB: 10, 4-MET: 4, DEABA: 0.7 | E: 11.2 D: 14.4 |

The abbreviations used in Table 3 refer to the following compounds.

3G: triethylene glycol dimethacrylate
CQ: camphorquinone
DEABA: N,N'-dimethylaminobenzoic acid
4-MET: 4-methacryloxyethyl trimellitic acid Examples 28–33

Predetermined amounts of polymerizable monomers and a polymer powder shown in Table 4 were weighed and mixed to form a solution or a dispersion, and the mixture was stored in a constant-temperature box at 45° C. and then visually observed for a change in flowability to evaluate the storage stability of the composition.

The compositions in Examples visually showed no clear change in flowability, and exhibited excellent storage stability.

TABLE 4

| | Polymerizable monomers (g) | | Polymer (g) |
|---|---|---|---|
| Example 28 | 2.6E: 5, MMA: 8, | HEMA: 3, 4-META: 2 | MSH: 2 |
| Example 29 | 2.6E: 5, MMA: 8, | HEMA: 3, 4-META: 2 | PMS: 2 |

TABLE 4-continued

| | Polymerizable monomers (g) | | Polymer (g) |
|---|---|---|---|
| Example 30 | 2.6E: 5, MMA: 8, | HEMA: 3, 4-META: 2 | MSB: 2 |
| Example 31 | 2.6E: 5, MMA: 8, | HEMA: 3, 4-META: 2 | PMS: 2 MSB: 1 |
| Example 32 | 2.6E: 5, MMA: 8, | HEMA: 3, 4-META: 2 | PMMA: 1 MSB: 1 |
| Example 33 | 2.6E: 5, MMA: 8, | HEMA: 3, 4-META: 2 | PVAc: 2 |

Effect of the Invention

According to the present invention, there can be provided an adhesive composition which is easy to handle and gives an excellent restoration effect in the restoration treatment of a tooth, so that adhesion dental treatment can be reliably carried out.

What is claimed is:

1. An adhesive composition for dental treatment comprising
   (A) 98 to 60 parts by weight of a polymerizable monomer mixture containing 2 to 20% by weight of a monomer having acidic group, said monomer having acidic group being selected from the group consisting of monomers containing sulfonic acid group and monomers containing carboxylic acid group or anhydride thereof,
   (B) 2 to 40 parts by weight of a polymer, said polymer being at least one polymer selected from the group consisting of (b1) a copolymer obtained from alkyl (meth)acrylate, a styrene monomer and a hydroxyalkyl (meth)acrylate whose molecule contains at least one hydroxyl group, (b2) a copolymer obtained from alkyl (meth)acrylate and a styrene monomer, (b3) a copolymer obtained from alkyl (meth)acrylate, a styrene monomer and butadiene, (b4) polyvinyl acetate, and (b5) a combination of a polyalkylacrylate and at least one of the polymers (b1), (b2), (b3) and (b4), and
   (C) 0.01 to 35 parts by weight of a polymerization initiator,
   provided that the total amount of the components (A), (B) and (C) is 100 parts by weight.

2. An adhesive composition for dental treatment comprising
   (A) 98 to 60 parts by weight of a polymerizable monomer mixture containing 2 to 20% by weight of a monomer having acidic group, said monomer having acidic group being selected from the group consisting of monomers containing sulfonic acid group and monomers containing carboxylic acid group or anhydride thereof,
   (B) 2 to 40 parts by weight of a polymer, wherein said polymer can form a solution or dispersion having the property that the solution or dispersion of 10 parts by weight of the polymer in 90 parts by weight of methyl methacrylate shows a viscosity of 100 cps or less at 25° C., and
   (C) 0.01 to 35 parts by weight of a polymerization initiator,
   provided that the total amount of the components (A), (B) and (C) is 100 parts by weight.

3. An adhesive composition for dental treatment comprising
   (A) 98 to 60 parts by weight of a polymerizable monomer mixture containing 2 to 20% by weight of a monomer having acidic group, said monomer having acidic group being selected from the group consisting of monomers containing sulfonic acid group and monomers containing carboxylic acid group or anhydride thereof, (B) 2 to 50 parts by weight of a polymer, wherein said polymer (B) is at least one polymer selected from the group consisting of (b1) a copolymer obtained from alkyl (meth) acrylate, a styrene monomer and a hydroxyalkyl (meth)acrylate whose molecule contains at least one hydroxyl group, (b2) a copolymer obtained from alkyl (meth)acrylate and a styrene monomer, (b3) a copolymer obtained from alkyl (meth)acrylate, a styrene monomer and butadiene, (b4) polyvinyl acetate, and (b5) a combination of a polyalkylacrylate and at least one of the polymers (b1), (b2), (b3) and (b4), and wherein said polymer (B) can form a solution or dispersion having the property that the solution or dispersion of 10 parts by weight of the polymer in 90 parts by weight of methyl methacrylate shows a viscosity of 100 cps or less at 25° C., and (C) 0.01 to 35 parts by weight of a polymerization initiator, provided that the total amount of the components (A), (B) and (C) is 100 parts by weight.

4. The adhesive composition of claim 1 or 2, wherein the polymerization monomer mixture contains further 5 to 30% by weight of at least one monomer selected from the group consisting of (meth)acrylate containing hydroxyl group and acrylate having ethylene glycol chain in the molecule.

5. The adhesive composition of claim 1, wherein the polymerizable monomer mixture contains 10 to 50% by weight of a polyfunctional acrylate.

6. The adhesive composition of any one of claims 1 to 3, wherein the monomer having acidic group is a 4-(meth) acryloxyethyltrimellitic acid or its acid anhydride.

7. The adhesive composition of claim 1 or 2, wherein the polymerizable monomer mixture (A) comprises (a1) 2 to 20% by weight of 4-(meth)acryloxyethyltrimellitic acid or its acid anhydride, (a2) 5 to 25% by weight of 2-hydroxylalkyl acrylate, (a3) 10 to 50% by weight of at lease one di(meth)acrylate selected from the group consisting of di(meth)acrylate having urethane bond, di(meth) acrylate containing aromatic group and di(meth)acrylate having ethylene glycol chain, and (a4) 10 to 60% by weight of alkyl(meth)acrylate.

8. The adhesive composition of claim 1 or 2, wherein the polymerization initiator is a photopolymerization initiator, an alkylborane or partially oxidized alkylborane.

9. The adhesive composition of claim 1, wherein the adhesive composition contains a filler (D) in addition to the components (A), (B) and (C) in an amount of 25 to 400 parts by weight per 100 parts by weight of the total amount of the components (A), (B) and (C).

10. The adhesive composition of claim 4, wherein the monomer having acidic group is 4-(meth) acryloxyethyltrimellitic acid or its acid anhydride.

11. The adhesive composition of claim 1, wherein the components (A) to (C) are separated into at least two compositions in a liquid or paste state for storage, said at least two compositions being mixed immediately prior to use.

12. The additive composition of claim 9 wherein the components (A) to (D) are separated into at least two compositions in a liquid or past state for storage, said at least two compositions being mixed immediately prior to use.

* * * * *